(12) United States Patent
Kaler et al.

(10) Patent No.: US 6,333,200 B1
(45) Date of Patent: Dec. 25, 2001

(54) MINIATURIZED IMMUNOSENSOR ASSEMBLED FROM COLLOIDAL PARTICLES BETWEEN MICROPATTERNED ELECTRODES

(75) Inventors: Eric W. Kaler; Orlin D. Velev, both of Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/358,494

(22) Filed: Jul. 21, 1999

Related U.S. Application Data
(60) Provisional application No. 60/094,173, filed on Jul. 27, 1998.

(51) Int. Cl.[7] .................................................. G01N 33/543
(52) U.S. Cl. ...................... 436/518; 435/7.1; 435/287.2; 422/68.1; 422/82.01; 422/82.02; 204/194; 204/411
(58) Field of Search ..................... 204/194, 411; 422/68.1, 82.01, 82.02; 435/7.1, 287.2; 436/518

(56) References Cited

U.S. PATENT DOCUMENTS
5,137,827 * 8/1992 Mroczkowski et al.

* cited by examiner .

*Primary Examiner*—Bao-Thuy L. Nguyen
(74) *Attorney, Agent, or Firm*—Connolly Bove Lodge & Hutz LLP

(57) ABSTRACT

The invention is a sensor for the presence of bio-specific (e.g., immunological) molecules. It is aimed to giving an alternative, highly advanced method for performing different tests for the presence of immuno-specific molecules in liquid environments such as body liquids, biological cultures, environmental samples, etc. Gold patterns are photolithoghraphyically fabricated onto glass substrates to form addressable electrodes of micron size. The sensor is assembled when colloidal particles from suspension are deposited dielectrophoretically in the microscopic gaps between the electrodes. The surfaces of these particles carry immuno-active binding sites that collect the target molecules. The sensor readout is accomplished by secondary tagging of the target molecules with colloidal gold and its enhancement by silver nucleation, which leads to short-circuiting of the electrodes. The device allows extreme miniaturization and direct electric readout. We anticipate detection levels as low as $10^{-21}$M, which is a 200 times gain in sensitivity over the conventional techniques.

1 Claim, 7 Drawing Sheets

Figure 1:
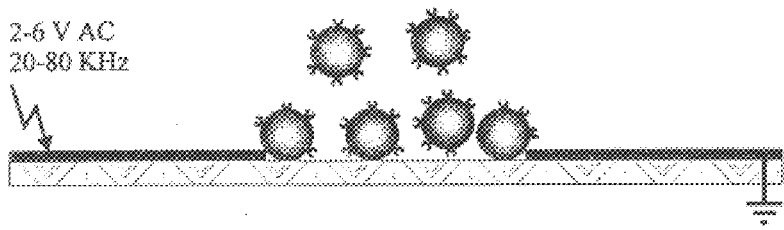
Figure 1:
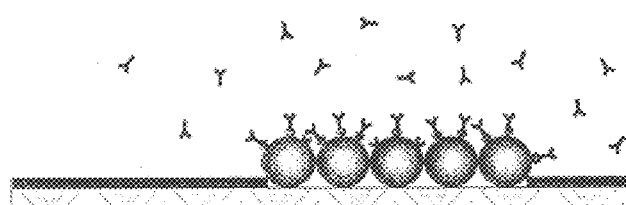
Figure 1:
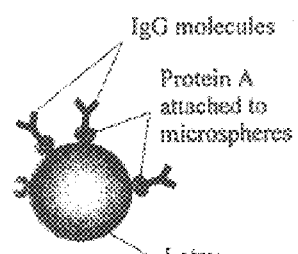
Figure 1:
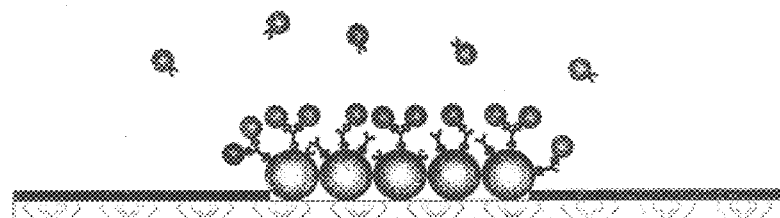
Figure 1:
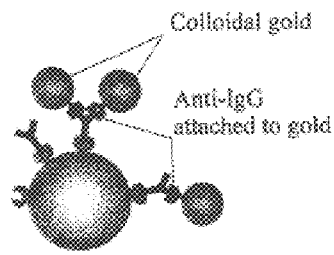
Figure 1:

(4 of 7 Drawing Sheet(s) Filed in Color)

Scheme of a basic unit 1"x1" in size.
The mask is 2"X2" and features 4 basic units
that differ only by the gap between the electrodes
Scale 7:1, all dimensions are in millimeters.

Mask Design v. 2.1
Page 1 of 3
<u>Single Basic Unit</u>
Velev, Kaler 01.98 a b $a$ $b$ a b

MINIATURIZED IMMUNOSENSOR ASSEMBLED FROM COLLOIDAL PARTICLES BETWEEN MICROPATTERNED ELECTRODES

CROSS REFERENCE OF RELATED APPLICATION

This application is based upon provisional application Ser. No. 60/094,173, filed Jul. 27, 1998.

BACKGROUND

Immunological tests for specific diseases, pathogens or allergens are routinely used in hospitals, laboratories, food, drug and environmental control, and are typically carried out by latex agglutination. They constitute a multi-billion dollar industry, which is surging at present due to the increased demand for better health care and environmental quality. These tests are typically preformed by means of latex agglutination assays, a simple and versatile tool for immunodetection (Bangs. L. B., in "Liquid and Surface-Borne Particle Measurement Handbook", Knapp, J. Z., Barber, T. A., Lieberman, A., Eds., Marcel Dekker, N.Y. 1996). These tests however have a number of disadvantages, including the need for relatively large amount of sample, the ambiguous optical readout, and the unsuitability for miniaturization, automation and electronic readout.

While the above drawbacks and the impending computerization of clinical procedures have called for electronic immunosensors, the progress in this area is still quite modest. The sensors available today are either too complex and difficult to use (e.g., based on total internal reflection) or too specific and narrowly oriented (e.g., enzyme catalysis) to be widely usable.

Our invention described here provides general means to replace the agglutination assays used today with high-tech, yet cheap sensors, which can simultaneously test for presence of different molecules in very small samples and give results that are directly read by a computer. The invention is applicable to nearly all of the immunological tests available today, and can be extended to testing for DNA fragments and other genetic markers.

SUMMARY OF THE INVENTION

The invention is a sensor for the presence of bio-specific (e.g. immunological) molecules. It is aimed to giving an alterative, highly advanced method for performing different tests for the presence of immuno-specific molecules in liquid environments such as body liquids, biological cultures, environmental samples, etc. At first, gold patterns are photolithographically fabricated onto glass substrates to form addressable electrodes of micron size. The sensor is assembled when latex particles from suspension are deposited dielectrophoretically in the microscopic gaps between the electrodes. The surfaces of these particles carry immuno-active binding sites that collect the target molecules. The sensor readout is accomplished by secondary tagging of the target molecules with colloidal gold and its enhancement by silver nucleation, which leads to short-circuiting of the electrodes. The device allows extreme miniaturization and direct electric readout.

DESCRIPTION OF THE FIGURES ENCLOSED

The File of this patent contains at least one drawing executed in color. Copies of this patent with color drawings will be provided by the Patent and Trademark Office upon request and payment of the necessary fee.

FIG. 1. Schematics of the main stages of sensor assembly and functioning. The procedure is illustrated by an immunoglobulin test, but modifications for other types of tests are possible.

Figure 2:
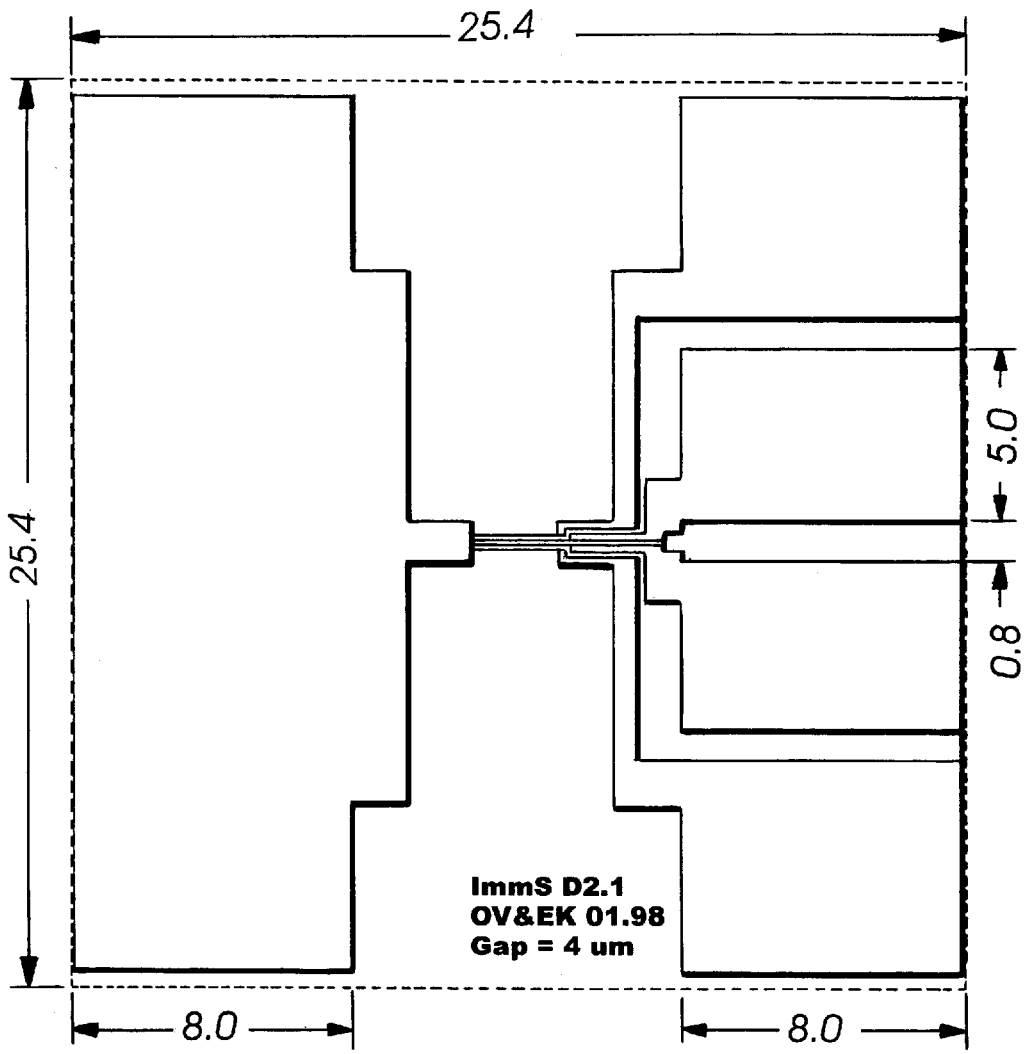

FIG. 2. Design of the photolithography mask of a four-electrode pattern.

Figure 3:
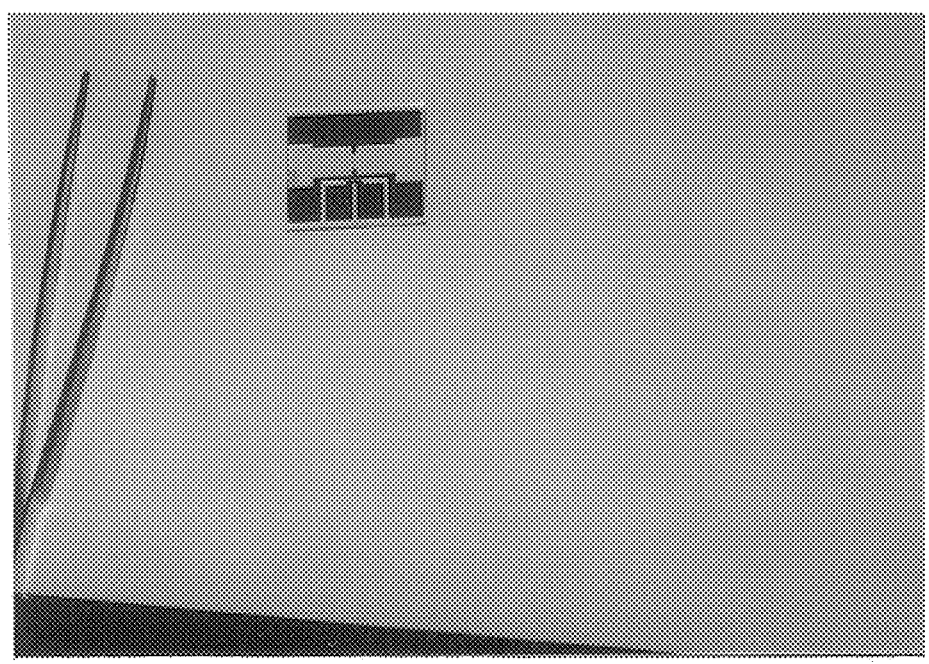
Figure 3:
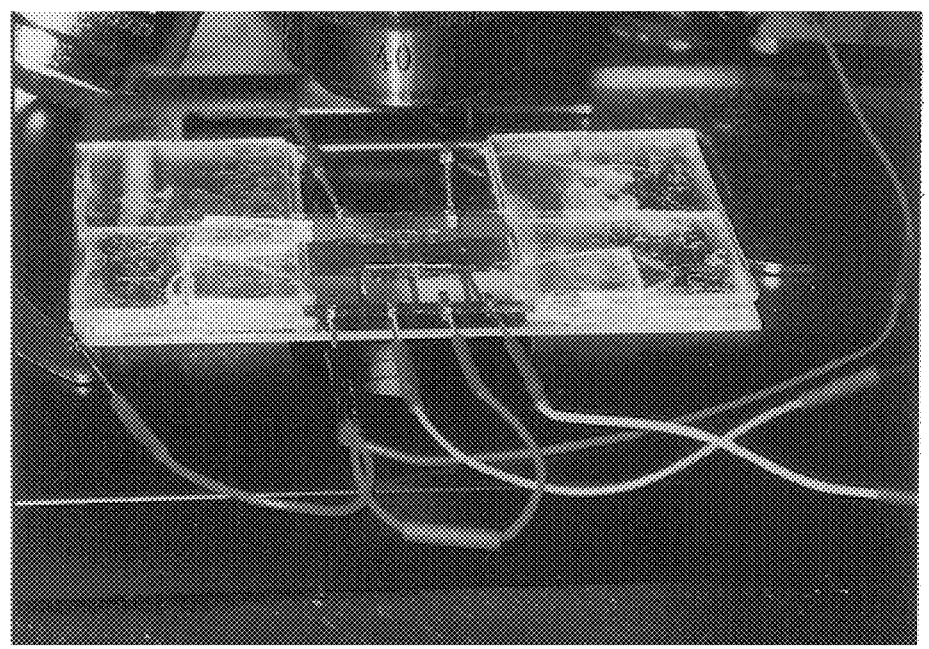

FIG. 3. (a) Photograph of a single "chip" as the ones used in the experiments. (b) View of the core of the experimental set-up used. A microscopic chamber is assembled over and around the active area in the center. The chip is mounted on the microscope stage and electric leads are attached to the four addressable electrodes in front and to the grounded ones in the back.

Figure 4:
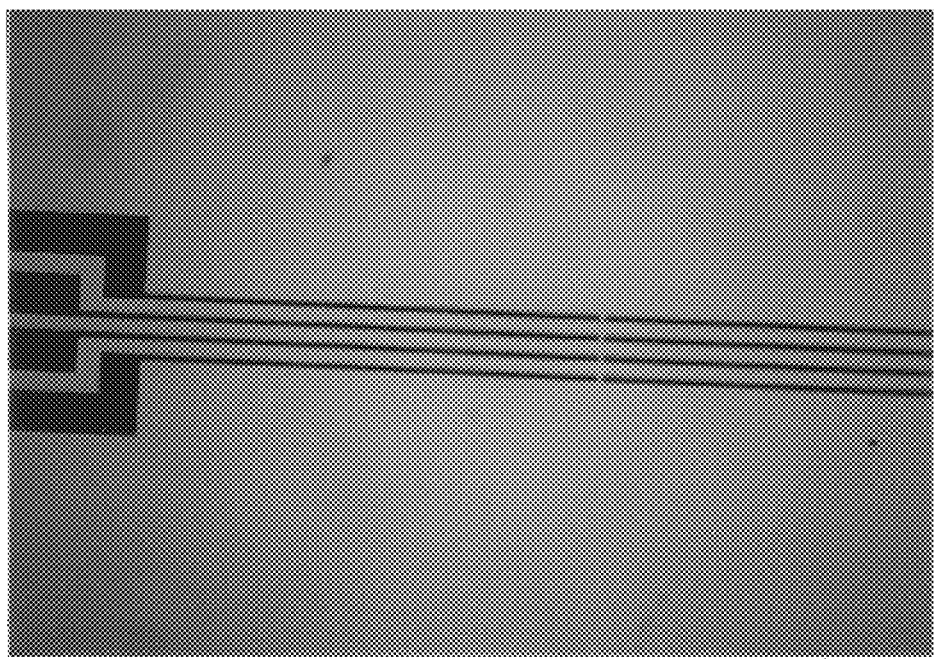
Figure 4:
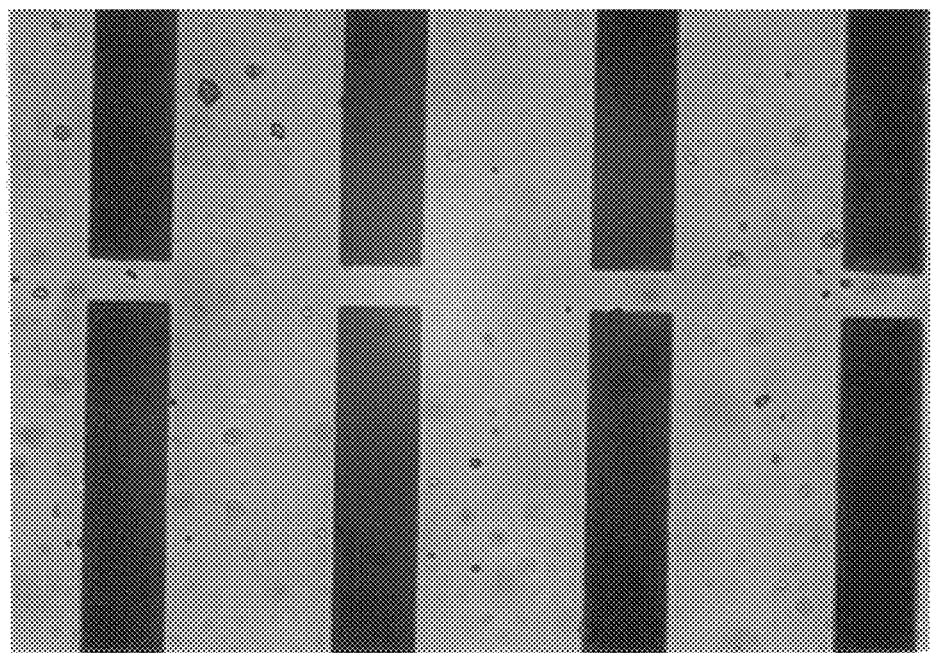

FIG. 4. (a) Low magnification and (b) high magnification view of the active area of the sensor as seen through the microscope.

Figure 5:
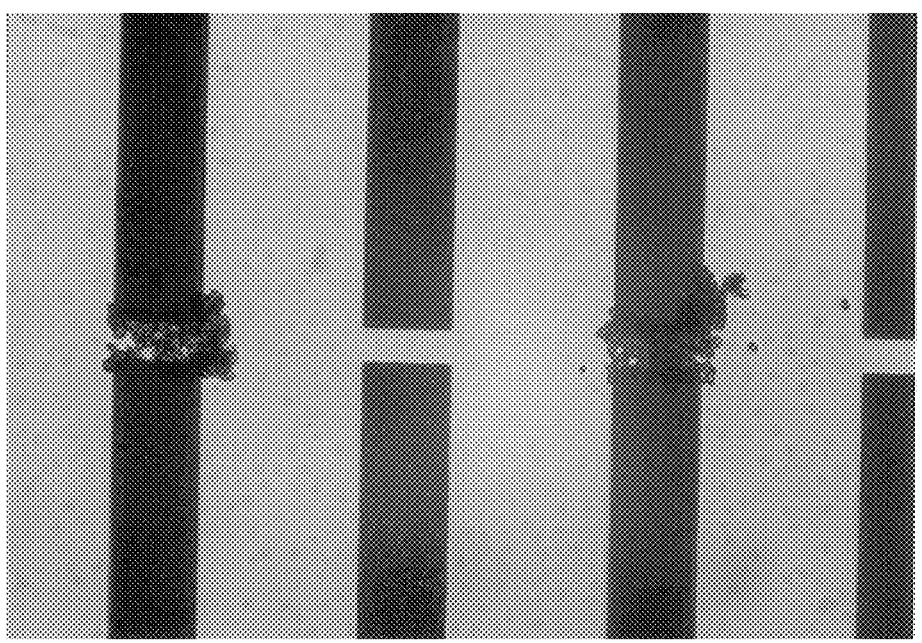
Figure 5:
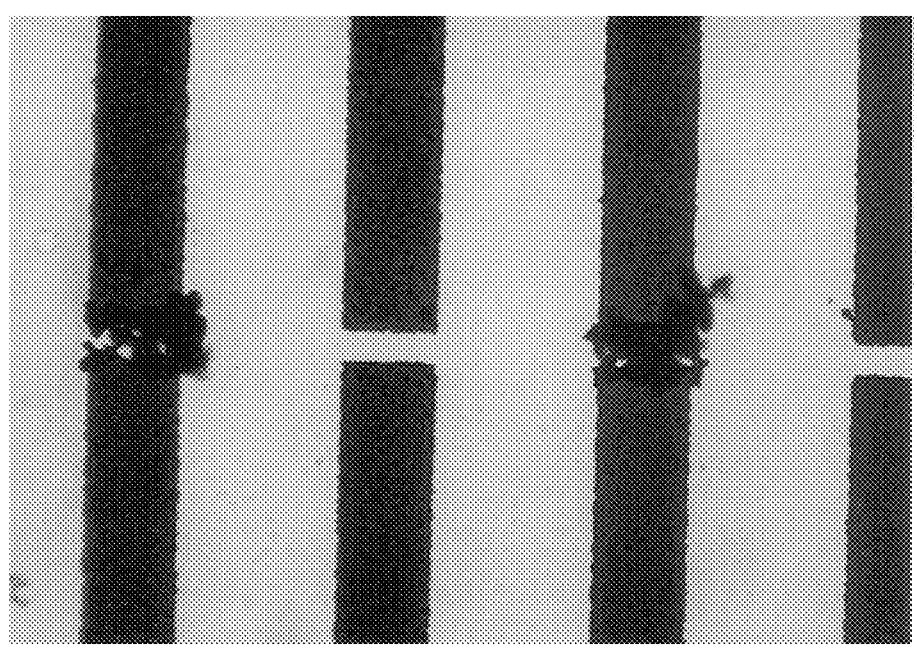

FIG. 5. Photographs of the sensor area during an experimental run. (a) Particles have been collected by AC field between the $1^{st}$ and $3^{rd}$ electrodes and coagulated; magnetic, protein A covered latex has been used in this example. (b) the same chip after the particles have been treated with human IgG, tagged with goat anti-human IgG gold colloid, and silver stained. It is seen that the electrodes have become short-circuited by the metal layer (black) deposited around the latex. Note the low background—metal deposition occurs only on the immuno-specific areas.

Figure 6:
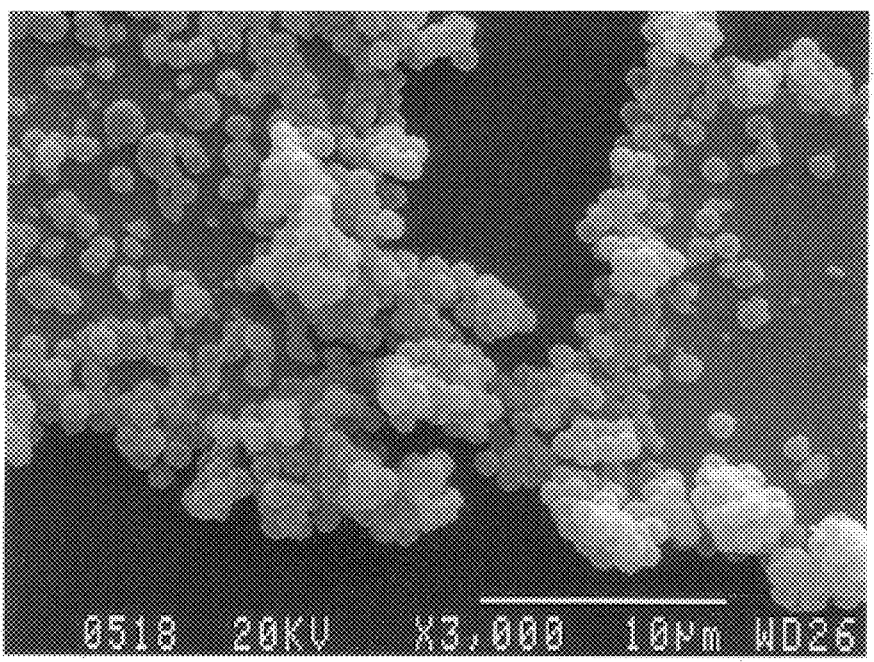
Figure 6:
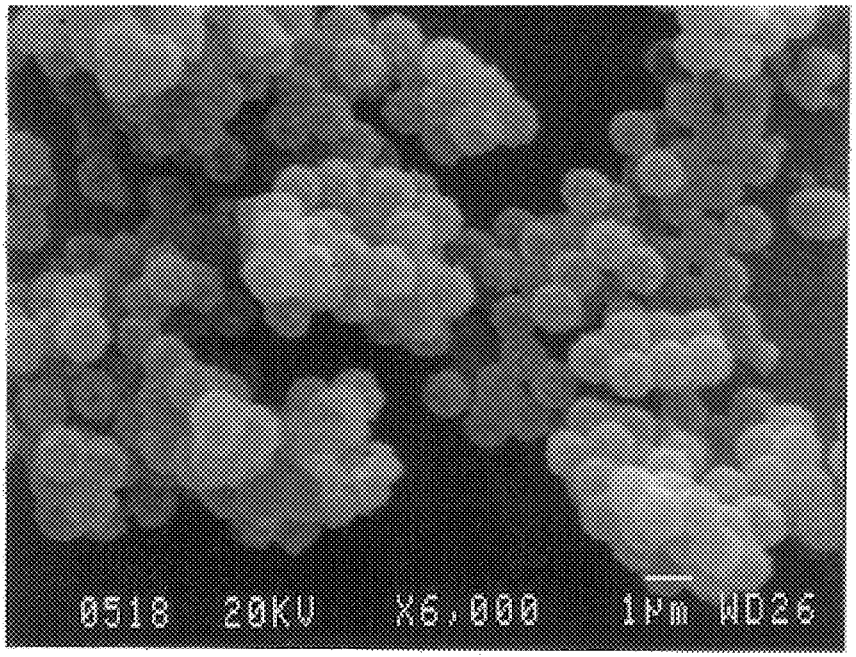

FIG. 6. SEM micrographs at two different magnifications of the gold-tagged and silver-enhanced latex particles between the electrodes (a positive IgG-specific experiment). It is seen, that the particles are encrusted in grainy metal layer, which makes them conductive and short-circuits the electrodes.

Figure 7:
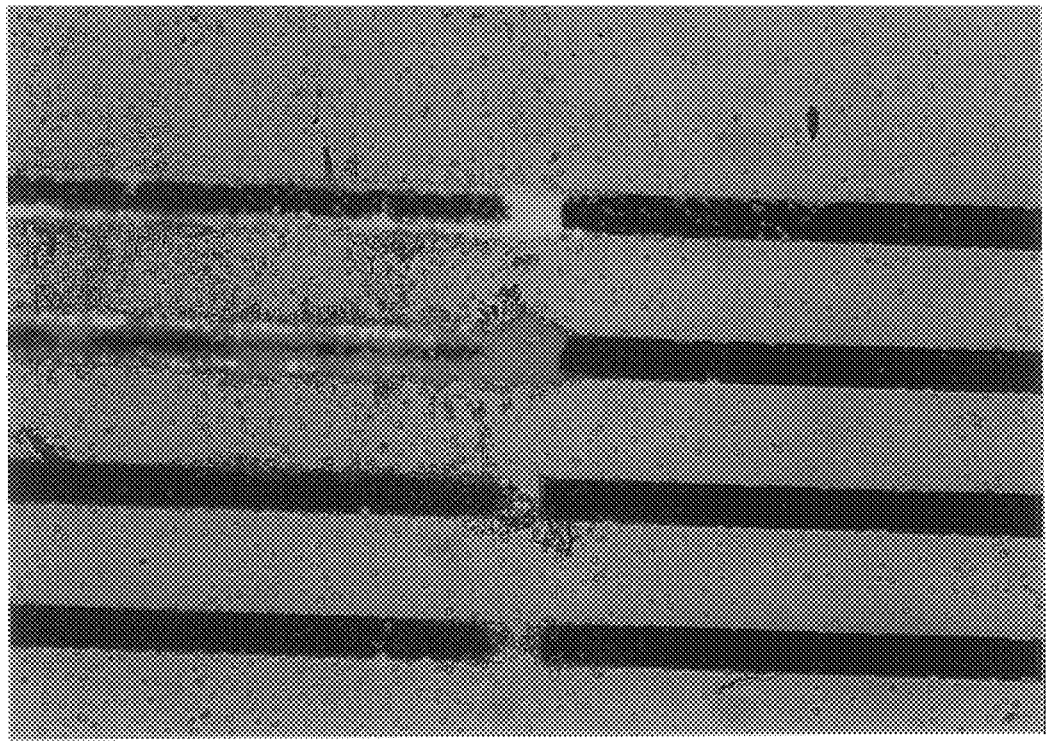

FIG. 7. An illustration of the ability of the method to assemble different types of particles in the gaps between the individually addressable electrodes. Two different fluorescent latexes (with red and green emission) have been used. One of the latexes was deposited between a pair of the electrodes first; followed by washing and deposition of another type of latex between another pair of electrodes. Photograph taken in mixed transmitted/fluorescence illumination mode.

DESCRIPTION OF THE PRINCIPLE AND THE EXPERIMENTAL RESULTS

The schematics of the principal main stages involved in the assembly and functioning of the immunosensor invented is presented in FIG. 1. Micron-sized gold stripes are deposited onto a glass substrate to create a pattern of thin electrodes with small gaps between them. The active area of the sensor is then created in situ by deposition of latex particles, covered with a bio-specific molecule, typically a protein. Such particles are widely available and relatively cheap due to their application in agglutination assays. In the majority of our experiments, the latexes were covered with Protein A, which binds to the Fc portion of the human immunoglobulin (IgG) molecules. To collect and deposit the latex microspheres exactly in the small gap between the electrodes, the effect of dielectrophoresis (Pohl, H. A., "Dielectrophoresis" Cambridge Univ. Press. 1978; Fuhr, G. et. al., Naturwissencschaften 81. 5218.194) is used. The particles, typically suspended in low-electrolyte aqueous solution are subjected to an alternating electric field of frequency between 20–80 KHz and amplitude of 2–6 V. The optimal dielectrophoretic conditions depend on the type of the particles used and are determined experimentally. After the microspheres are collected in the gaps, they are coagulated by applying an appropriate agent—strongly dilute solutions of cationic surfactants, metal ions, or in some cases even pure water. The nature and concentration of the appropriate substance is a function of the type of the latex and its surface functionality. The electric field is turned off after particle coagulation. The assembled sensors are washed in an environment close to the one in which the bio-specific interaction occurs. This concludes the preparation stage of the sensors.

In the user stage of an experiment, the assembled sensors are incubated in contact with media that may carry the immuno-specific molecules. Thus, if human IgG was present, it was collected by the Protein A molecules to form a strongly and specifically attached secondary protein around the particles. The readout of the test results is carried out by tagging with colloidal gold and silver-enlargement of the particles (Hayat, M. A., Ed., Immunogold-silver staining: principles, methods and applications, CRC Press. Boca Raton, Fla., 1995) to short-circuit the electrodes. The procedures used include: (i) washing of the sensor area to remove the excess unbound IgG, (ii) incubation with a suspension of colloidal gold conjugated to a secondary antibody—in our case goat anti-human IgG. After this stage, the particles are surrounded by strongly and specifically bound shell of colloidal gold particles, (iii) washing of the sensor area to remove the unbound gold particles and eventual fixation by a glutaraldehyde. (iv) silver enhancement—treatment with solution which deposits a silver layer on top of the gold particles, thus enlarging and fusing them together. (v) final wash with pure water and readout of the resistance between the electrodes. If the test results are positive, by this step the electrodes will be short-circuited.

Shown are figures with some of the results from our experiments. The substrate for our sensor was created by photolithographic techniques, similar to the ones widely used today in the fabrication of electronic and computer chips. The design of the photolithographic mask of a basic "chip" is presented in FIG. 2. The masks and the photolithography were made by specialized contractors. The final samples were prepared onto glass substrates with 2 nm Ti and 150 nm Au layers deposited (FIG. 3a). In the experiments, the sensor chips were attached to a special holder onto the microscope stage, and electric leads to the electrodes were attached to the edges (FIG. 3b). A small flow-though chamber with volume of approximately 10 $\mu$l was assembled on top of the electrode active area with adjacent small "corrals" for liquid insertion and removal formed by stripes of hydrophobic wax. Optical low-magnification and high magnification images of the active sensor area as seen through the microscope are presented in FIG. 4.

The Protein A covered latex microspheres used comprise encapsulated magnetic material in the bulk. These spheres could be collected between the electrodes by moderate magnitude AC fields (1–3 V) even in an environment, which contains modest levels of electrolyte. The coagulation of the particles in the gaps could be achieved simply by washing with deionized water. Photographs of the electrode gap area with bridges of particles deposited between two of the addressable electrode pairs are shown in FIG. 5. The sensor area is then washed with phosphate buffered saline (PBS) containing also BSA and Tween 20, and is incubated for 15 min with 250 $\mu$g/ml solution of human IgG. The sensor is washed with PBS again and incubated for 45 min with diluted suspension of 5 nm colloidal gold conjugated to goat anti-human IgG. The sensor is then washed, briefly treated with glutaraldehyde and silver-enhanced for 10 min with an electron microscopy enhancing reagent. The excess silver enhancer is removed by washing with distilled water before result readout.

The results of a positive IgG test can be easily detected by measuring the resistance between the electrodes, which typically is 30–70$\Omega$. This electric readout of the test is simple and reliable and is preserved indefinitely. Microscopic observations demonstrate that the latex particles in the test are heavily darkened, which indicates a high degree of silver deposition onto the attached gold particles (FIG. 5b). Scanning electron microscope (SEM) observations of the particles in the bridges demonstrate that the latex is covered by a grainy metal shell, as should be expected to result from the above procedure. Alternatively we have demonstrated that when a "negative" test is carried out, by removing either the IgG, or replacing the colloidal gold with a non-immunospecific sample, the resistance readout is either infinity or at least 10 times higher than in a "positive" experiment. Thus, we believe to have proven that the principles and the method presented here work and could be used in practical immunosensors.

To substantiate the claim for the universality of our method, we also carried out experiments with another pair of specifically interacting molecules—biotin and streptavidin, whereas the biotin was attached to the latex and the streptavidin to the gold. The results of the positive and the negative tests were similar to the ones outlined above. We have also proven, that the method could in principle be used to assemble multiple different sensors by addressing the individual electrode pairs one at a time. Thus we managed to assemble bridges from two types of fluorescent latex particles between two different electrode pairs on the same chip—FIG. 7.

Immunological tests for specific diseases, pathogens or allergens are routinely used in hospitals, laboratories, food, drug and environmental control and others and are typically carried out by latex agglutination. They constitute a multi-billion dollar industry, which is surging at present due to the increased demand for better health care and environmental quality. Our invention provides general means to replace the agglutination assays with high-tech, yet cheap sensors, which can simultaneously test for presence of different molecules in very small samples and give results that are directly read by a computer. The invention can also be applied to tests for DNA fragments and other genetic markers.

The most important new features of the sensor and of the method for its preparation are:

1. The application of the commercially available functionalized latex particles as an active element in an electrically read sensor.
2. The use of the dielectrophoretic force for the assembly of the microscopic active element onto photolithographically produced electrode design.
3. The use of functionalized colloidal gold particles as a promoter of the electrode short-circuiting in a positive immunological event.
4. The application of sliver enhancer reagent, followed by water rinse as the means to implement the electrode short-circuit and obtain the positive readout.
5. The formulation of the whole method as a sequence of the above and other intermediate procedures, to assemble and utilize the immunosensor.
6. The further modification of the method to produce on a single microscopic chip a number of individually addressable elements sensitive to different immunomolecules.

The invention has the following advantages over the existing agglutination methods:
1. Extreme miniaturization of the active sensor area.
2. Extreme sensitivity of the sensor in terms of the minute amount of the sample and the small number of specific molecules required to trigger the sensor. The theoretical sensitivity of the method is more than 200 times higher than the theoretical sensitivity of the agglutination assays (an estimate of the sensitivity is applied separately).
3. The possibility to assemble and operate simultaneously on a single chip multiple sensors for different molecules.
4. Direct and simple electric readout of the test results in by measuring the resistance. This reduces the risk of perceptive human error, and allows direct input of the data into a computer.
5. The method could be used to replace ail of the latex agglutination tests available today, as it is not limited to any specific biomolecule.
6. The disposable sensor chips and the readout equipment could be fabricated at a reasonably low price by today's technology and do not require special alignment or skills from the operators.

Estimation of the Sensitivity of the Proposed Miniaturized Immunosensor

TABLE 1

Estimated sensitivity of the agglutination immunological tests used presently - literature data *.

| Parameter | Realistic estimate | Theoretical limits |
|---|---|---|
| Microsphere diameter, μm | 1.0 | 10 |
| Sensitivity, number of molecules | $10^8$ | $10^5$ |
| Sensitivity, M | $10^{-16}$ | $10^{-19}$ |

* Data from Bangs, L. B., in "Liquid and Surface-Borne Particle Measurement Handbook", Knapp, J. Z, Barber, T. A., Lieberman, A., Eds., Marcel Dekker, NY, 1996.

Sensitivity of Our Proposed Miniaturized Immunosensor

The following formula has been derived and used for the estimates $$S = N_p C_f \frac{4r_p^2}{(r_g S_f)^2}$$

where

S is the estimated sensitivity in number of molecules.

$N_p$ is the number of particles attached between the electrodes.

$C_f$ is the fractional coverage of the surface required to short-circuit the electrodes.

Conservative estimates of 0.5–0.75 were used.

$r_p$ is the radius of the latex particles used in the sensor assembly.

$r_g$ is the radius of the gold particles being attached to the surface of the latex particles.

$S_f$ is the factor of enlargement of the gold particles by the silver enhancement reagent.

The producers claim an enlargement in the order of tens of times, but we have used a conservative estimate of 3–5 times.

TABLE 2

Estimated sensitivity of our proposed immunosensor *.

| Parameter | Conservative estimate | Optimistic estimate |
|---|---|---|
| $N_p$ | 16 | 16 |
| $C_f$ | 0.75 | 0.5 |
| $r_p$, nm | 400 | 200 |
| $r_g$, nm | 5 | 10 |
| $S_f$ | 3 | 5 |
| Sensitivity, S, number of molecules | $3.5 \times 10^5$ | $5 \times 10^2$ |
| Sensitivity, M | $5 \times 10^{-20}$ | $10^{-21}$ |

* Both of the above estimates are much more conservative than the theoretical limit which is a few tens of molecules.

Comparing Tables 1 and 2 shows, that our proposed method has a gain in sensitivity of at least 200 times over the conventional technique.

What is claimed is:

1. A miniaturized immunosensor comprising:

a) substrate having fabricated patterns forming micro electrodes having microscopic gaps there between, b) colloidal latex particles dielectrophoretically deposited in said microscopic gaps, said particles having thereon biospecific molecules that specifically bind and collect target molecules.

* * * * *